US010754932B2

(12) United States Patent
Wiederspohn et al.

(10) Patent No.: US 10,754,932 B2
(45) Date of Patent: Aug. 25, 2020

(54) CENTRALIZED CONSENT MANAGEMENT

(71) Applicant: SAP SE, Walldorf (DE)

(72) Inventors: Joerg Wiederspohn, Heidelberg (DE); Volker Lehnert, Walldorf (DE); Carsten Pluder, Sankt Ingbert (DE); Bjoern Christoph, Walldorf (DE)

(73) Assignee: SAP SE, Walldorf (DE)

( * ) Notice: Subject to any disclaimer, the term of this patent is extended or adjusted under 35 U.S.C. 154(b) by 302 days.

(21) Appl. No.: 15/636,677

(22) Filed: Jun. 29, 2017

(65) Prior Publication Data

US 2019/0005210 A1    Jan. 3, 2019

(51) Int. Cl.
| | |
|---|---|
| G06Q 10/10 | (2012.01) |
| G06Q 30/02 | (2012.01) |
| G06Q 30/06 | (2012.01) |
| G06Q 10/04 | (2012.01) |
| G06Q 10/06 | (2012.01) |
| G06F 21/31 | (2013.01) |
| G16B 50/00 | (2019.01) |
| G16H 10/60 | (2018.01) |
| G06F 21/62 | (2013.01) |
| G06Q 50/24 | (2012.01) |
| G06Q 50/18 | (2012.01) |
| G16H 40/20 | (2018.01) |

(52) U.S. Cl.
CPC .......... *G06F 21/31* (2013.01); *G06F 21/6245* (2013.01); *G06Q 10/10* (2013.01); *G06Q 50/24* (2013.01); *G16B 50/00* (2019.02); *G16H 10/60* (2018.01); *G06Q 50/18* (2013.01); *G16H 40/20* (2018.01)

(58) Field of Classification Search
CPC ........ G06Q 10/10; G06Q 50/24; G06Q 50/18; G06F 21/31; G06F 21/6245; G16H 10/60; G16H 40/20; G16B 50/00

USPC ........................................ 705/1.1–912, 317
See application file for complete search history.

(56) References Cited

U.S. PATENT DOCUMENTS

| | | | | |
|---|---|---|---|---|
| 7,076,558 B1 * | 7/2006 | Dunn | ................. | G06F 21/6218 709/225 |
| 7,269,853 B1 | 9/2007 | Dunn | | |
| 7,912,971 B1 * | 3/2011 | Dunn | .................. | H04L 63/102 709/203 |

(Continued)

FOREIGN PATENT DOCUMENTS

WO    WO 01/33936 A2    5/2001

OTHER PUBLICATIONS

Gigya Data Sheet, "Gigya's Customer Identity Management Platform," Jun. 2015, pp. 1-2. (Year: 2015).*
SAP News Center, "SAP to Acquire Gigya, Market Leader in Customer Identity and Access Management," Sep. 24, 2017. (Year: 2017).*

(Continued)

*Primary Examiner* — Jonathan P Ouellette
(74) *Attorney, Agent, or Firm* — Fish & Richardson P.C.

(57) ABSTRACT

A consent management system (CMS) manages a number of individual consent data records of data subjects. The CMS stores predefined consent templates to be instantiated when an individual consent data record is created. The CMS represents a centralized system for management of individual consent data records that are created, stored, and maintained in relation to provided consent by data subjects for purposes of operations related to stored personal data records by associated application systems. The CMS may run on an on-premise, cloud, or personal device computing platform.

20 Claims, 12 Drawing Sheets

(56) References Cited

U.S. PATENT DOCUMENTS

| | | | |
|---|---|---|---|
| 9,047,228 B2 | 6/2015 | Sarferaz et al. | |
| 9,280,684 B1* | 3/2016 | Kragh | G06F 16/245 |
| 10,372,483 B2* | 8/2019 | Beiter | G06F 9/468 |
| 2004/0133454 A1* | 7/2004 | Desio | G06F 17/243 |
| | | | 705/2 |
| 2006/0178913 A1* | 8/2006 | Lara | G16H 40/20 |
| | | | 705/3 |
| 2012/0151557 A1* | 6/2012 | Ahmed | G06F 21/604 |
| | | | 726/2 |
| 2012/0254320 A1 | 10/2012 | Dove et al. | |
| 2015/0213195 A1 | 7/2015 | Blechman | |
| 2016/0112208 A1* | 4/2016 | Williams | H04L 9/006 |
| | | | 713/158 |
| 2016/0301764 A1 | 10/2016 | Ruback et al. | |
| 2016/0350339 A1 | 12/2016 | Lehnert et al. | |
| 2017/0140174 A1* | 5/2017 | Lacey | G06F 21/6245 |
| 2019/0253431 A1* | 8/2019 | Atanda | G06F 21/62 |

OTHER PUBLICATIONS

Zinck, Barb Mosher, "Gigya Helps Manage Connected Consumer," CMS Wire, Jun. 5, 2013. (Year: 2013).*

Extended European Search Report for European Application No. 17001772.7, completed Dec. 15, 2017; Munich; 6 pages.

InterComponentWare Inc.; "ICW Patient Consent Manager"; retrieved online; 2 pages; (http://exploredoc.com/doc/9013865/icw-patient-consent-manager).

Wikipedia; "Consent management"; retrieved online Jun. 28, 2017; 2 pages; (https://en.wikipedia.org/wiki/Consent_management).

Regulation (EU) 2016/679 of the European Parliament and of the Council of Apr. 27, 2016; retrived online Jun. 28, 2017; 88 pages; (http://eur-lex.europa.eu/eli/reg/2016/679/oj).

Ryan van Leent; "(Multi-channel) Citizen Engagement"; published Jul. 11, 2016; retrieved online Jun. 28, 2017; 5 pages; (https://blogs.sap.com/2016/07/11/multi-channel-citizen-engagement/).

* cited by examiner

200

Consent Template Name 202

Tenant ID 204
Template ID 206
Template Version 208
Model 210
Purpose 212
Controller Properties 214
Application Properties 215
Term Properties 216
Control Properties 218
Layout Properties 220
Access & Transfer Properties 222
3rd Party Recipients Properties 224
Validity Period Properties 226
System Administrative Properties 228
Lifecycle Status 230

Consent 302

Tenant ID 304
Consent ID 306
Template ID 308
Template Version 310
Controller 312
Valid-From 314
Valid-To 316
Data Subject (Ref to) 318
Data Subject Formatted Description 320
3rd Party Recipient Records 322
System Administrative Attributes 324
Renewal Records 326
Withdrawal Record 328
Consent Status 330
Lifecycle State 332
Copy Flag 334
Original Consent (Ref To) 336
Model 338
Purpose 340
Application 341
Access Type 342
Transfer Type 344
Term 346

FIG. 3

CENTRALIZED CONSENT MANAGEMENT

BACKGROUND

Personal data means information relating to an identified or identifiable natural person (e.g., data subject). An identifiable person is one who can be identified, directly or indirectly, in particular by reference to an identifier such as a name, an identification number, location data, online identifier or to one or more factors specific to the physical, physiological, genetic, mental, economic, cultural or social identity of that person. Processing of personal data is regulated by law. For example, a panoply of federal privacy-related laws including, among others, The Federal Trade Commission Act (15 U.S.C. §§ 41-58) (FTC Act), The Financial Services Modernization Act (Gramm-Leach-Bliley Act (GLB)) (15 U.S.C. §§ 6801-6827), The Health Insurance Portability and Accountability Act (HIPAA) (42 U.S.C. § 1301 et seq.), The Electronic Communications Privacy Act (18 U.S.C. § 2510), and the Computer Fraud and Abuse Act (18 U.S.C. § 1030) regulates collection and use of personal data in United States of America (USA). A data protection directive (official Directive 95/46/EC on the protection of individuals with regard to the processing of personal data and on the free movement of such data) regulates the processing of personal data within European Union (EU). Directive 95/46/EC is due to be replaced by General Data Protection Regulation (GDPR) (Regulation (EU) 2016/679) on May 25, 2018.

In accordance with law regulations, personal data of a data subject (e.g., a customer) may be collected by a data controller (e.g., a company) based on criteria of lawful processing of personal data. For example, lawful processing of personal data may be performed in relation to performance of a contract, a legal obligation, etc. A natural or legal person, public authority, agency or any other entity which alone or jointly with others determines purposes and means of the processing of the personal data can be referred to as data controller. Alternatively, personal data may be collected based on consent. The consent is an informed consent for the data controller provided by the data subject to processing of personal data in written or electronic form. Companies often run analytical processes on personal data that they possess to gain information and to improve decision making regarding strategic, tactical, and operational activities. Normally, the personal data is blocked for access or deleted after primary purpose and legal retention time is over.

BRIEF DESCRIPTION OF THE DRAWINGS

The claims set forth the embodiments with particularity. The embodiments are illustrated by way of examples and not by way of limitation in the figures of the accompanying drawings in which like references indicate similar elements. The embodiments, together with its advantages, may be best understood from the following detailed description taken in conjunction with the accompanying drawings.

FIG. 2 is an exemplary data model of a consent template, according to one embodiment.

FIG. 3 is an exemplary data model of a consent, according to one embodiment.

DETAILED DESCRIPTION

Figure 1:
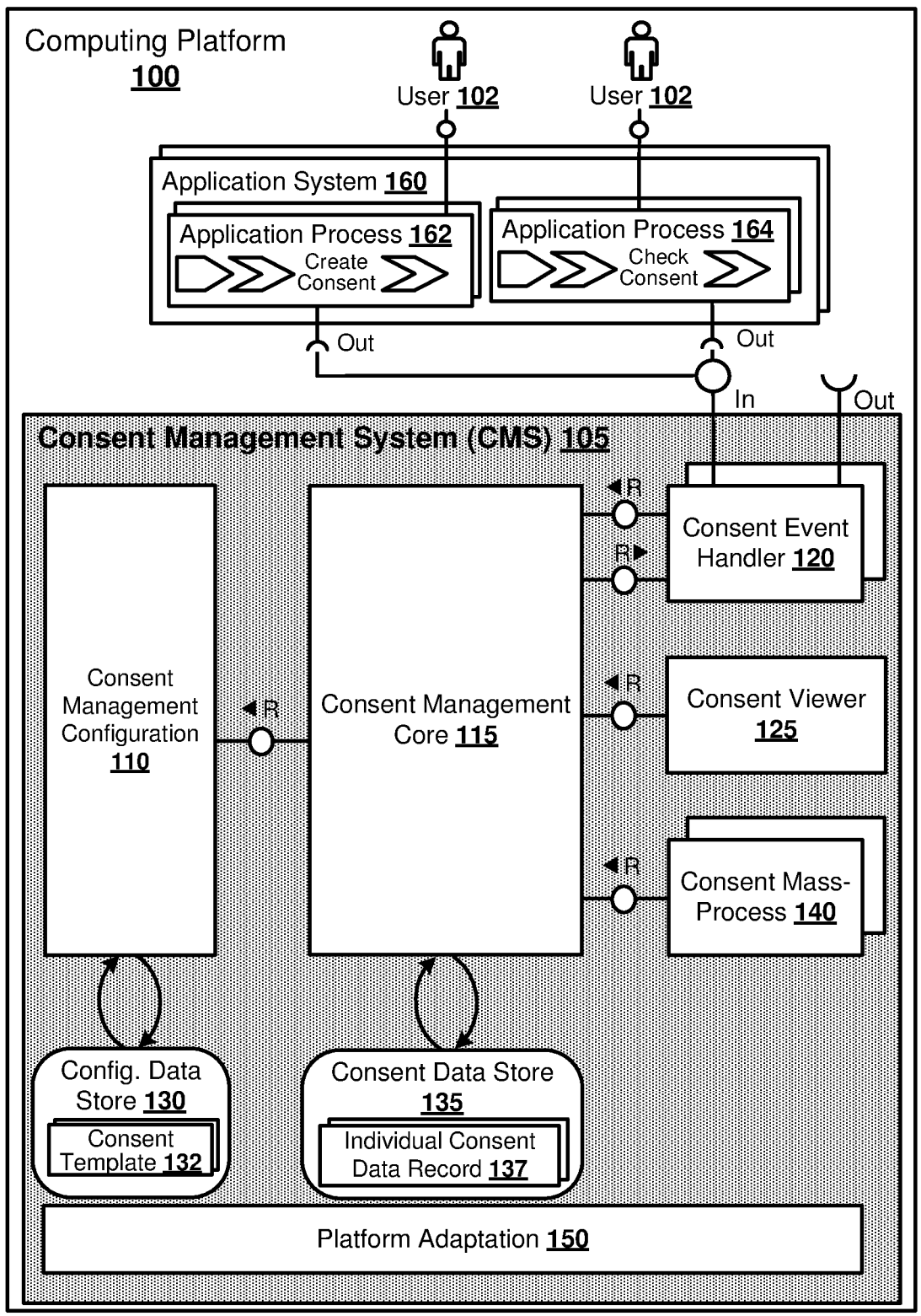
FIG. 1 is a block diagram illustrating a computing platform including a consent management system (CMS), according to one embodiment.

Embodiments of techniques for centralized consent management are described herein. In the following description, numerous specific details are set forth to provide a thorough understanding of the embodiments. One skilled in the relevant art will recognize, however, that the embodiments can be practiced without one or more of the specific details, or with other methods, components, materials, etc. In other instances, well-known structures, materials, or operations are not shown or described in detail.

Reference throughout this specification to "one embodiment", "this embodiment" and similar phrases, means that a particular feature, structure, or characteristic described in connection with the embodiment is included in at least one of the one or more embodiments. Thus, the appearances of these phrases in various places throughout this specification are not necessarily all referring to the same embodiment. Furthermore, the particular features, structures, or characteristics may be combined in any suitable manner in one or more embodiments.

Normally, acquired personal data, such as customer-related data acquired by companies, is blocked for accessing or deleted after primary purpose use or when legal retention time is over.

Typically, personal data (e.g. customer-related data), including consent data records, is collected by computer-implemented application systems configured to collect, store, manage, and interpret data associated with activities related to a data subject associated with the personal data. A consent data record represents a single consent given by the data subject through a computer-implemented application system. The consent data record corresponds to one data subject and to one computer-implemented application system. The consent data record may be uniquely identified based on a corresponding data subject and computer-implemented application system. However, the collected consent data is restricted to domains of the application systems. Subsequent processing of the personal data outside of the application systems' domains does not have access to the consent data records to prove consent and therefore cannot be performed lawfully.

Application systems and processes are increasingly provided by a processor of a cloud platform, and often in combination with on-premise application systems. In such scenarios, the consent data records are stored in different application systems, either the on-premise one or in the cloud. Similarly, subsequent on-premise or cloud platform processes do not have access to the consent data records stored at the other system. As the consent data records are scattered across multiple systems, it is challenging for the data subject to manage and/or withdraw consent.

At least some of the technologies described herein address these problems by providing a centralized consent management system (CMS) that may run on on-premise and cloud computing platforms to exchange individual consent data records of data subjects between on-premise computing platforms and cloud computing platforms, and by providing a personal consent repository (PCR) for management of individual consent data records associated with the data subject operating the PCR. The CMS system may send notifications for consent events to third party recipients and provide capabilities to create, check, renew or withdraw consent.

FIG. 1 illustrates a computing platform 100 including a CMS 105 and a number of application systems such as application system 160, according to one embodiment. The CMS 105 and the number of application systems are deployed and run on the computing platform 100. It should be appreciated, however, that the number of application systems may be deployed and running on one or more computing platforms different from the computing platform 100. The CMS 105 and the number of application systems utilize services and resources provided by the computing platform 100. For example, the services provided by the computing platform 100 to tenants of the computer platform 100 may include application development environment, runtime environment, database management services, user management services, etc. A group of users of the computing platform 100 that share common rights to access a specific instance (e.g., a service instance, an application system instance) provided by the computer platform 100 can be referred to as a tenant of the computing platform 100. The computing platform 100 may be a cloud platform, an on-premise web application server platform or a personal device platform such as a personal computer, mobile device, etc.

In one embodiment, the CMS 105 includes consent management configuration component 110 and configuration (config.) data store 130. The consent management configuration component 110 communicates with the config. data store 130 to read and write configuration data. The configuration data includes configuration settings of the CMS 105. The configuration settings may be stored in configuration entities such as consent templates and code lists such as lists of languages, lists of countries, lists of purposes, lists of data controllers etc. within the config. data store 130. For example, the database management services provided by the computing platform 100 may be utilized to store the configuration entities in database tables of a database (not illustrated) associated with the config. data store 130. The database may be part of the computing platform 100. It should be appreciated, however, that the database may also be external to the computing platform 100 and may be connected to the computing platform 100 through a network such as the Internet or an Intranet of an organization.

In one embodiment, the configuration data may include predefined code lists (either extensible or not). A code list includes codes and code descriptions. For example, a language code list may include codes with one or more digits for languages and language names as code descriptions. Such one or more digit language codes and corresponding language names may form pairs of codes and code descriptions such as (AF, Afrikaans), (AR, Arabic), (HY, Armenian), etc. The code lists may refer to standardized classifying nomenclatures defined by the International Organization for Standardization (ISO). For example, the language code list may refer to standardized nomenclature for classifying languages ISO 639-1. The code descriptions may be defined in different languages to ensure multi-language support. Examples of code lists include, but are not limited to, list of languages, list of countries, list of purposes, list of applications, list of consent controls, list of access types to consent data records (internal, by data subject, by third parties), list of transfer types of consent data records (no transfer, to data subject, to third parties), list of template lifecycle states (inactive, active, deprecated), list of consent statuses (initial, agreed, disagreed, withdrawn), list of consent data records' lifecycle states (initial, active, expiring, expired, blocked), list of third party recipients, and list of data controllers. The consent management configuration component 110 may provide a user interface (UI) (not illustrated) for entering the configuration data. For example, the UI may be provided to users of the CMS 105 authorized to configure the CMS 105 (e.g., CMS administrators/specialists). The consent management configuration component 110 may provide the functionality of reading and writing configuration data to other components of the CMS 105 as a local service of the computing platform 100 via a local application programming interface (API).

In one embodiment, the consent management configuration component 110 provides a functionality to define one or more consent templates. When the CMS 105 is running, the one or more consent templates may be instantiated by the number of application systems associated with the CMS 105 to create individual consent data records for data subjects. For example, users of the number of application systems may trigger creation of the individual consent data records. The individual consent data records are created for the users of the number of application systems when the users are the data subjects. It should be appreciated, that the users of the number of application systems may create individual consent data records for other data subjects (not illustrated). The individual consent data records for the data subjects may be created based on the one or more consent templates. The individual consent data records may refer to data records that store data (e.g., including personal data and category of personal data such as sensitive or not-sensitive) provided by the data subjects through the number of application systems. The data records that store the data are stored separately from the individual consent data records. For example, in a dedicated database for the data records, different from the database for the individual consent data records.

In one embodiment, consent template 132 is defined via the consent management configuration component 110. For example, the consent template 132 may be created via the local service provided by the consent management configuration component 110 and stored in the config. data store 130. In one embodiment, the consent template 132 is instantiated by the application system 160 to create an individual consent data record for a data subject. In one embodiment, user 102 of the application system is the data subject. It should be appreciated, however, that the user 102 may not be the data subject. Rather, the user 102 may be authorized to create individual consent data records for one or more data subjects (e.g., the user 102 may be legally authorized to create individual consent data records on behalf of one or more data subjects). For example, application process 162 "create consent" of the application system 160 may trigger the instantiation of the consent template 132. The individual consent data record may be associated with consent given for processing of personal data of the user 102 in relation to the application system 160. One or more consent templates such as the consent template 132 may be relevant for the application system 160 when creating individual consent data records for data stored by a data controller through the application system 160. Further, the consent template 132 is defined for the application system 160. An exemplary data model of a consent template is described in detail below, with reference to FIG. 2.

In one embodiment, the consent management core component 115 communicates consent management configuration component 110. The consent management core component 115 provides a functionality to create, read, update, and delete individual consent data records. The consent management core component 115 may include a UI (not illustrated) that allows data subjects to access corresponding individual consent data records. A data subject registered as user of the CMS 105 may view, renew, or withdraw one or more individual consent data records corresponding to the data subject through the UI. In one embodiment, the consent management core component 115 reads configuration data including consent templates via the local service of the consent management configuration component 110. For example, the consent management core component 115 may read the consent template 132 from the config. data store 130 via the consent management configuration component 110. The consent management core component 115 may provide the functionality to create, read, update, and delete individual consent data records to other components of the CMS 105 as a service local to CMS 105 via a local/internal API.

In one embodiment, the consent management core component 115 communicates with consent data store 135 to read and write individual consent data records, based on consent templates, to the consent data store 135. For example, the consent management core component 115 may create and store individual consent data record 137 based on the consent template 132. An individual consent data record identifies consent given by a data subject to an application system to process data associated with the data subject, such as personal data of the data subject, in association with a functionality of the application system. The consent template 132 may be instantiated by the application system 160 when the user 102 accesses the application system 160. At instantiation, the user 102 may be asked to agree or disagree to give consent. For example, a question text included in the consent template 132 may be displayed on a UI (not illustrated) of the application system 160. The question may specify a purpose, based on which the personal data of the data subject to be processed, and request consent from the user 102. Further, the displayed UI of the application 160 may provide the user 102 with one or more UI controls to enable the user 102 to agree or disagree to give the consent. When the user agrees to give consent, an individual consent data record is stored in the consent data store 135. An exemplary data model of an individual consent data record is described in detail below, with reference to FIG. 3.

In one embodiment, the consent data store 135 may store one or more individual consent data records, including the individual consent data record 137, as database records. For example, the database management services provided by the computing platform 100 may be utilized to store the database records in database tables of a database (not illustrated) associated with the consent data store 135. The database may be part of the computing platform 100. It should be appreciated, however, that the database storing the data records may also be external to the computing platform 100 and may be connected to the computing platform 100 through a network such as the Internet or an Intranet of an organization. The database records may be stored in the database associated with the config. data store 130, as described above.

In one embodiment, the consent management core component 115 is in communication with consent viewer 125, consent event handler components 120, and consent mass-process components 140. The consent viewer 125 provides functionality to display individual consent data records of the data subjects to authorized users of the CMS 105. For example, a data protection auditor may be registered as an authorized user of the CMS 105 and may be given access rights to view individual consent data records of the data subjects in the CMS 105. Further, the consent viewer 125 may provide a dedicated UI for selecting, based on criteria, individual consent data records to be displayed. The individual consent data records may be selected based on criteria associated with data controller, data subject, purpose, template, etc. The consent viewer 125 may read the individual consent data records from the consent data store 135 through the local service of the consent management core component 115 and select certain individual consent data records to be displayed for the authorized user based on the criteria.

In addition, the consent management core component 115 communicates with consent event handler components 120. In one embodiment, the consent event handler components 120 handle inbound events and outbound events. The inbound events may be triggered by services invoked by entities external to the CMS system 105, such as the application system 160. Examples of services that may be invoked from outside include services associated with consent instantiation, consent creation (e.g., through the "create consent" application process 162"), checking for individual consent data records (e.g., through "check consent" application process 164 of the application system 160"), viewing of individual consent data records, consent renewal, consent withdrawal, etc. The outbound events may be triggered by services invoked by the consent management core component 115. Examples of services invoked by the consent management core component 115 include notification for new individual consent data record, notification for expiring consent, and notification for expired consent.

In one embodiment, when the individual consent data record 137 is created and stored in the consent data store 135, the consent management core component 115 invokes an outbound event notification for a new individual consent data record. In one embodiment, one or more consent mass-process components 140 may send service messages or process other transactions associated with the individual consent data record 137. For example, when the individual consent data record 137 is withdrawn (e.g., by invoking the consent withdrawal inbound service), consent status of the individual consent is set to "withdrawn" and the individual consent data record is updated in the consent data store 135. A "withdrawn" consent mass-process component of the consent mass-process components 140 may check for newly "withdrawn" individual consent data records on a defined period (e.g., by storing a timestamp indicating a timepoint of last prior check and checking consent data records modified after the timepoint) and may trigger consequential activities for newly "withdrawn" consent data records. Examples for such activities include terminating validity of the newly "withdrawn" consent data records, setting a lifecycle status of the consent data record to "expired" and notifying the associated application system 160 that the consent has been withdrawn by the data subject. Similarly, an "expired"

consent mass-process component of the consent mass-process components 140 may select expired consent data records, for which a notification for expired consent has not been sent yet, and may send a notification for expired consent. As another example, when the individual consent record 137 is not withdrawn and not yet expired, but expiring, an "expiring" mass process component of the consent mass-process components 140 may send notification to notify the user 102 or the data subject that the individual consent data record 137 is expiring. The notification may include an option for renewal of the individual consent data record 137.

In one embodiment, the CMS 105 may include one or more consent report components (not illustrated). Consent report components may be components providing capability to select, evaluate, and output individual consent data records from the consent data store 135 or aggregate consent data on a report UI or to a file. For example, a report on key performance indicators (KPIs) including, but not limited to, aggregation of basic summaries and descriptive statistics of the consent data records stored in the consent data store 135 may be generated through the one or more consent report components. Another report may check for consistency of the consent data. Authorized users of the CMS 105 may schedule regular reports as well as request instant reports. To generate the reports, the consent report components may read, e.g., via the local API of the consent management core component 115, the individual consent data records stored at the consent data store 135. Alternatively, the consent report components may read the individual consent data records from the consent data store 135 via database capabilities provided by the computing platform 100. For example, via structured query language (SQL) queries.

In one embodiment, the CMS 105 includes platform adaptation component 150. Since services provided by the different types of computing platforms may differ, The CMS 105 may not operate efficiently on the different types of computing platforms. Thus, the platform adaptation component 150 adapts the CMS 105 to the computing platform 100 depending on a type of the computing platform 100 (e.g., on-premise, cloud, or personal device). For example, the platform adaptation component 150 may compensate differences in the services provided by the computing platform 100 running on-premise and the computer platform 100 running in the cloud or on a personal device. For example, the computing platform 100 running on-premise and the platform 100 running in the cloud or on a personal may utilize different database management services, different user management services, different user interface (UI) services, different security services, etc. Therefore, such service differences are to be compensated by the platform adaption component 150.

Further, some of the functionalities provided by the CMS 105 might not be necessary when the CMS 105 is deployed on certain types of computing platforms. For example, when the CMS 105 runs on a personal device as a PCR, the consent viewer 125 may not be necessary because the data subject accesses corresponding individual consent data records through the personal device, while individual consent data records of multiple data subjects cannot be reviewed by a data protection auditor through the CMS 105, when installed on the personal device computing platform.

FIG. 2 illustrates an exemplary data model 200 defined for a consent template, according to one embodiment. Based on the data model 200, one or more consent templates may be created and stored. For example, the consent template 132 may be created based on the data model 200. The consent template 132 may be defined for a tenant specified for one or more application systems. The consent template 132 may be defined for one purpose, for one data controller, and one or more languages. The one or more consent templates may be instantiated by application systems to create individual consent data records associated with stored data records provided by data subjects through the application systems. The one or more consent templates may be defined for a tenant that is defined for one or more application systems (e.g., the tenant of computing platform 100 described above with reference to FIG. 1). Therefore, for an application system, one or more consent templates may be relevant when creating individual consent data records for data stored by a data controller through the application system. An appropriate consent template from the one or more relevant consent templates may be selected (e.g., based on specified context) by the application system when creating an individual consent data record. The one or more consent templates may be created via local service provided by the consent management configuration component 110 of FIG. 1 and stored in the config. data store 130 of FIG. 1.

The data model 200 for consent template includes consent template name 202 and a number of other attributes describing characteristics of a consent given in relation to a data record associated with a data subject. In one embodiment, an attribute from the number of attributes may be preconfigured with a default attribute value. The default value may be added to an individual consent data record created from a consent template defined in accordance with the data model 200. In one embodiment, tenant ID 204, template ID 206, and template version 208 are key attributes of the consent template data model 200. Tenant ID attribute 204 specifies a tenant associated with the consent template and defined at the computing platform 100 of FIG. 1. Further, the template ID attribute 206 and the template version attribute 208 provide identification and versioning information for the consent template. The model attribute 210 defines a consent model of the consent template (opt-in or opt-out in the data model 200). The model attribute 210 determines whether data subjects are asked to explicitly accept a purpose, based on which personal data of the data subjects to be processed (opt-in) or whether the data subjects are asked to explicitly deny the purpose, based on which the personal data to be processed (opt-out).

In one embodiment, the consent template is defined for a certain purpose. The purpose attribute 212 specifies the purpose of the consent template. The purpose associated with the consent template defines purpose of processing personal data by the data controller that obtained the personal data. In one embodiment, purposes may be defined in a purpose code list including at least purpose ID (code) and purpose description (code description). For example, the purpose ID may be included in the individual consent data record 137 by the application system 160 to specify a specific purpose for processing the personal data of the data subject. The purpose description corresponding to the purpose ID in the purpose code list may be displayed on a UI when the individual consent data record is read from the consent data store 135. Further, controller properties attribute 214 specifies one or more data controllers that are authorized to process the personal data. A data controllers' code list includes information for the data controllers such as, but is not limited to, controller ID (code) and controller name (code description). For example, the controller ID is included in the individual consent data record 137 by the application system 160, when the application system 160 refers to a specific data controller. The controller name may be included when the individual consent data record 137 is read from the consent data store 135 to be displayed on the UI. Further, application properties attribute 215 specifies one or more application systems associated with the consent template. Optionally, the application properties attribute 215 may define authorizations for one or more application systems to access individual consent data records created based on the consent template.

In addition, term properties attribute 216 defines text phrases shown by a UI when the individual consent data records are created. The text phrases can be specified in different languages, based on languages configured to be supported by the consent template. For example, in case consent is requested from data subjects speaking different languages. Control properties attribute 218 defines controls and controls' text that must be displayed on the UI while creating the individual consent records. For example, a first button and a second button with labels "Agree" and "Disagree", respectively. Layout properties attribute 220 defines arrangement of the text phrases and the controls on the UI.

Moreover, access and transfer properties attributes 222 define whether the individual consent data records based on the consent template may be accessed by users from within an internal network of the data controller (e.g., "internal") or viewed by external users contracted to the data controller such as third-party organizations (access properties attribute). Further, the transfer properties attribute defines whether individual consent data records may be transferred and to whom. For example, when a value of the transfer properties attribute is set to "no transfer", an individual consent data record cannot be transferred to a third-party recipient. Third ($3^{rd}$) party recipients' properties 224 define a list of recipients to which the personal data associated with the individual consent data record is transferred, when transfer to $3^{rd}$ parties is allowed and the data subject provides consent at a later stage. Validity period properties 226 define how long the individual consent data record is valid upon creation of the individual consent data record. Additionally, the validity period properties 226 define a number of possible renewals of the individual consent data record (zero—"0"—when no renewal is possible) and expiration period. During the expiration period, notifications including an option to renew the consent may be sent to the data subject.

System administrative properties 228 define a set of properties that is common between CMS entities. Such properties include an identification of a user associated with the creation of the individual consent data record, creation date and time, an identification of a user associated with a change made for the individual consent data record, data and time of changes made for the individual consent data record. Lifecycle status attribute 230 is an object-specific attribute that describes lifecycle of a consent template. The lifecycle status attribute 230 of a consent template includes a number of states that may be defined such as inactive, active, deprecated.

FIG. 3 illustrates an exemplary data model 300 of consent 302, according to one embodiment. Individual consent data records of data subjects may be created in accordance with the data model 300. For example, the individual consent data record 137 of FIG. 1 may be created based on the data model 300. A consent is valid for a corresponding data controller. The individual consent data records include storing of consents which data subjects give to data controllers for certain purposes. When multiple controllers are specified in a consent (e.g., subsidiaries of a multi-national organization), an individual consent data record may be stored for each of the multiple controllers.

The consent 302 is associated with a tenant identified by tenant ID 304 (e.g., the tenant of the computing platform 100 of FIG. 1) and a unique consent ID 306. The consent 302 is based on a consent template specified by template ID 308 and refers to a version of the consent template (e.g., template version 310). For example, the consent 302 may be based on the consent template 132 of FIG. 1. A controller 312 attribute of the consent 302 refers to a data controller associated with the consent 302. The data controller requests the consent from a data subject. Valid-from 314 represents a date and time attribute specifying when validity of the individual consent 302 starts. Valid-to 316 is a date and time attribute specifying when the validity of the individual consent 302 ends. Data subject (Ref to) 318 specifies the data subject asked for the consent 302. For example, the user 102 of the application system 160 may be asked for the consent 302 The data subject (Ref to) 318 represents a reference to a data subject record/identification originally maintained in another system. Thus, the data subject (Ref to) 318 includes data for the other system, object type of the data subject (e.g., customer, supplier, employee, etc.), ID type and ID in the other system. The data subject (Ref to) 318 reference is unique and refers to exactly one record in the other system. Data subject formatted description 320 includes, for example, a name and postal address of the data subject.

In addition, $3^{rd}$ party recipient records 322 include a list of $3^{rd}$ party recipients as defined in the consent template and details for time and channel of transferring of personal data of the data subject. System administrative attributes 324 represent a set of attributes included in CMS entities such as the consent 302. Such administrative attributes include creation user, creation date and time, change user, change data and time, etc. Renewal records 326 specify time, data subject, and channel of renewing the consent 302. Similarly, withdrawal records 328 specify time, data subject, and channel of withdrawing the consent 302. Consent status 330 specifies status of the consent 302 from data subject perspective (e.g., initial, agreed, disagreed, withdrawn). Lifecycle state 332 is an object-specific attribute that represents lifecycle of an individual consent data record created in accordance with the data model 300 by instantiating the consent template 132 of FIG. 1. The lifecycle state 332 can be initial, active, expiring, expired, blocked. The consent status 330 and the lifecycle state 332 will be described in detail below with reference to FIG. 4 and FIG. 5, respectively.

Further, copy flag 334 marks the consent 302 as a copy of an original consent record. For example, when individual consent data records are exchanged with $3^{rd}$ party recipients, copies of the individual consent data records are sent to the $3^{rd}$ party recipients. As another example, copies of individual consent data records may be sent to other CMS system instances. When the consent 302 is a copy of an individual consent data record, copy flag 334 is marked and original consent (Ref to) 336 refers to the original individual consent data record. When the consent 302 is a copy of an individual consent data record, the copy consent 302 may not be changed within the CMS that stores the copy. Rather, original individual consent data record referred by original consent (Ref to) 336 may be changed (e.g., withdrawn or renewed). In addition, the template version 310 refers to consent model 338, consent purpose 340, consent access type 342, consent transfer type 344, and consent term 346. Application 341 attribute specifies the application system associated with the individual consent data record created in accordance with the consent data model 300.

Figure 4:
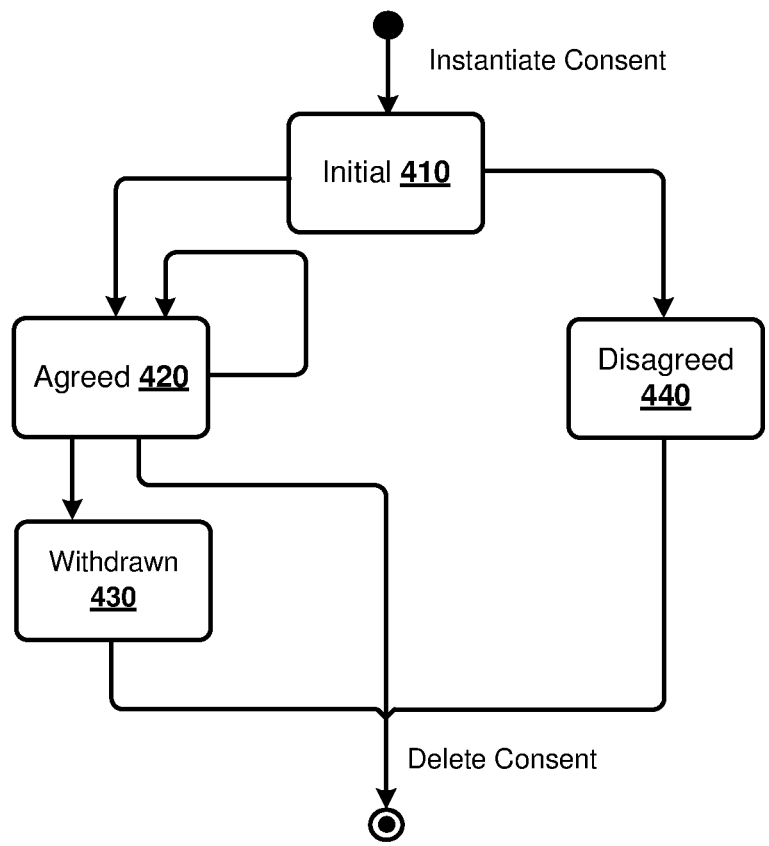
FIG. 4 is a state diagram illustrating consent statuses from a data subject perspective, according to one embodiment.

FIG. 4 illustrates consent statuses from a data subject perspective, according to one embodiment. State diagram 400 includes consent status "initial" 410, consent status "agreed" 420, consent status "withdrawn" 430, and consent status "disagreed" 440. When a consent template such as consent template 132 of FIG. 1 is instantiated to create an individual consent data record for the data subject (e.g., the individual consent data record 137 for the user 102 of FIG. 1), the data subject is asked to give consent. In one embodiment, the consent status is specified by a corresponding consent attribute (e.g., the consent status attribute 330 of FIG. 3).

In one embodiment, upon instantiation of the consent template, the consent status is set to "initial" 410. The consent status "initial" 410 is maintained until the data subject decides to agree or disagree to provide consent. When the data subject agrees to give consent, the consent status is set to "agreed" 420. Further, when expiration date of the consent approaches, the data subject may opt to renew the consent to maintain the consent status "agreed" 420. In one embodiment, the data subject opts to let the consent expire. In this case, the individual consent data record may be deleted.

Further, when the data subject decides to disagree to give the consent, the consent status is set to "disagreed" 440. Individual consent records with status "disagreed" may be deleted. In addition, the data subject may withdraw consents with status "agreed" 420. Upon withdrawal, the consent status is set to "withdrawn" 430. When the consent status is set to "withdrawn" 430 the individual consent record may be deleted.

Figure 5:
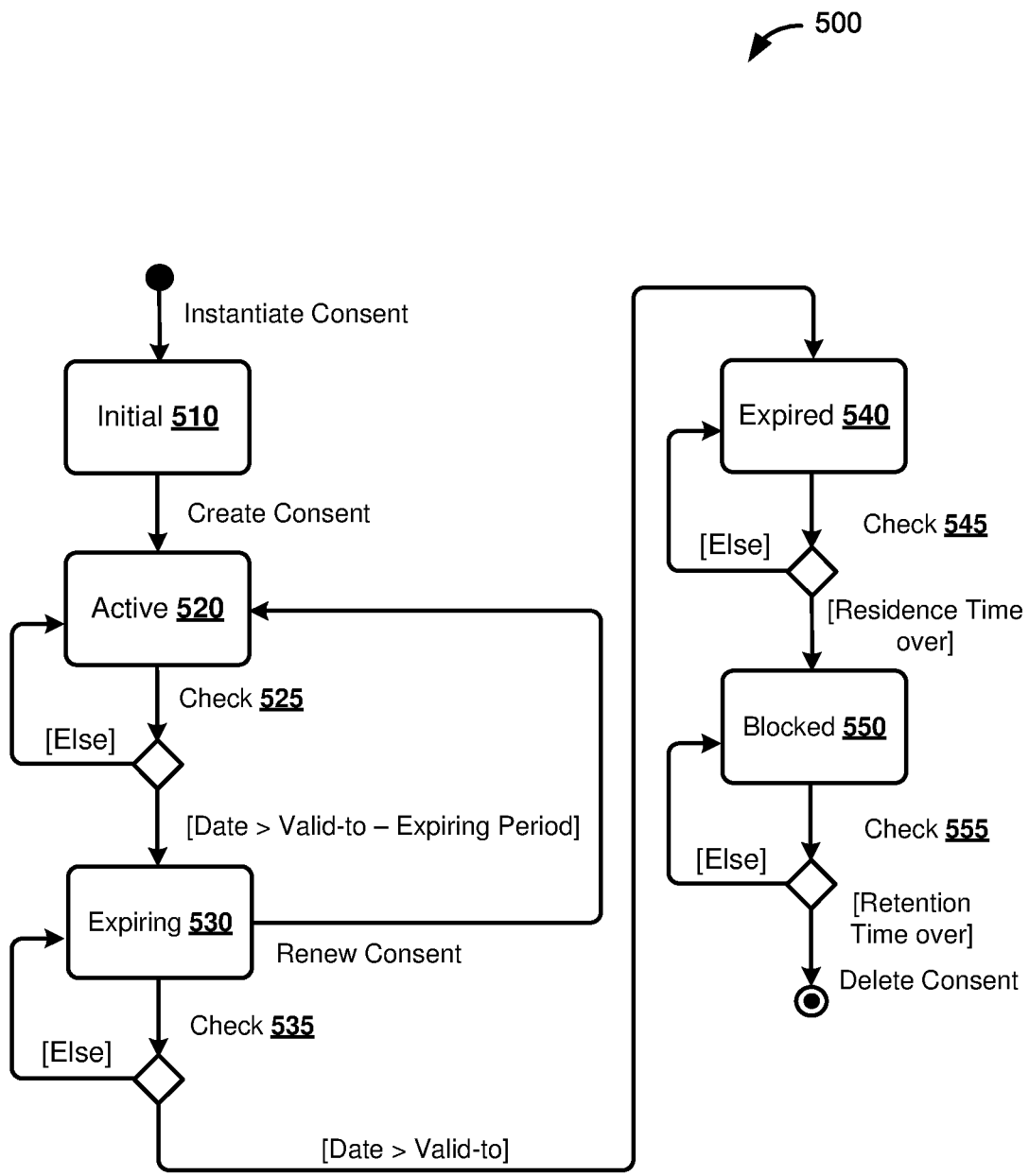
FIG. 5 is a state diagram illustrating an individual consent record lifecycle, according to one embodiment.

FIG. 5 illustrates lifecycle states of an individual consent data record such as the individual consent data record 137 of FIG. 1, according to one embodiment. State diagram 500 includes lifecycle state "initial" 510, lifecycle state "active" 520, lifecycle state "expiring" 530, lifecycle state "expired" 540, and lifecycle state "blocked" 550. In one embodiment, the lifecycle state of the individual consent data record is specified by a corresponding lifecycle attribute (e.g., lifecycle state attribute 332 of FIG. 3).

When a consent template is instantiated to create the individual consent data record, the lifecycle state of the individual consent data record is set to "initial" 510. Consequentially, when the individual consent data record is created and stored, the lifecycle state is set to "active" 520. Upon setting the lifecycle state to "active" 520, a check 525 is performed to determine whether the lifecycle state should be changed. For example, current date can be checked. In one embodiment, the current date is greater than a date specifying end of the validity of the individual consent data record (e.g., Valid-to attribute 316 of FIG. 3) minus expiring period (defined by validity period properties 226 of FIG. 2). Therefore, the lifecycle state of the individual consent data record is set to "expiring" 530. For example, in the consent template that is associated with an individual consent record the validity period may be defined as two (2) years from creation date and the expiring period in which expiring notifications should be sent out to the data subject may be defined as three (3) months prior to expiration date. Therefore, if the current date falls into the period three (3) months before expiration date of the individual consent data record, the lifecycle state of the individual consent record is set to "expiring" 530. Alternatively, the check 525 may determine that the current date is not greater than the date specifying the end of the validity of the individual consent data record minus the expiring period, and thus, the lifecycle state of the individual consent data record may remain "active" 520.

In one embodiment, when the lifecycle state of the individual consent data record is set to "expiring" 530, a check 535 is performed to determine whether the lifecycle state of the individual consent data record should be changed. In one embodiment, the current date is checked. When the current date is greater than the date specifying the end of the validity of the individual consent data record, the lifecycle state of the individual consent data record may be set to "expired" 540. Alternatively, the check 535 may determine that the current date is not greater than the date specifying the end of the validity of the individual consent data record, and thus, the lifecycle state of the individual consent data record may remain "expiring" 530. When the lifecycle state of the individual consent data record is "expiring" 530, renewing the individual consent data record may change the lifecycle state to "active" 520.

In one embodiment, when the lifecycle state of the individual consent data record is set to "expired" 540, a check 545 is performed to determine whether the lifecycle state of the individual consent data record should be changed. In one embodiment, residence time (if configured) is checked. The residence time may specify a residence period for keeping individual consent data records (accessible for users or data subjects) that have expired. When the residence time is over, the lifecycle state of the individual consent data record may be set to "blocked" 550. Blocked consent data records may not be accessed by the users or data subjects. However, the blocked consent data record may still be accessed by users with specific permissions, such as auditors/data privacy officers. Alternatively, the check 545 may determine that the residence time is not over, and thus, the lifecycle state of the individual consent data record may remain "expired" 540.

In one embodiment, when the lifecycle state of the individual consent data record is set to "blocked" 550, a check 555 is performed to determine whether the lifecycle state of the individual consent data record should be changed. In one embodiment, retention time is checked. The retention time specifies period for retaining blocked individual consent data records for legal purposes. When the retention time is over, the individual consent data record may be deleted. Alternatively, the check 555 may determine that the retention time is not over, and thus, the lifecycle state of the individual consent data record may remain "blocked" 550.

Figure 6:
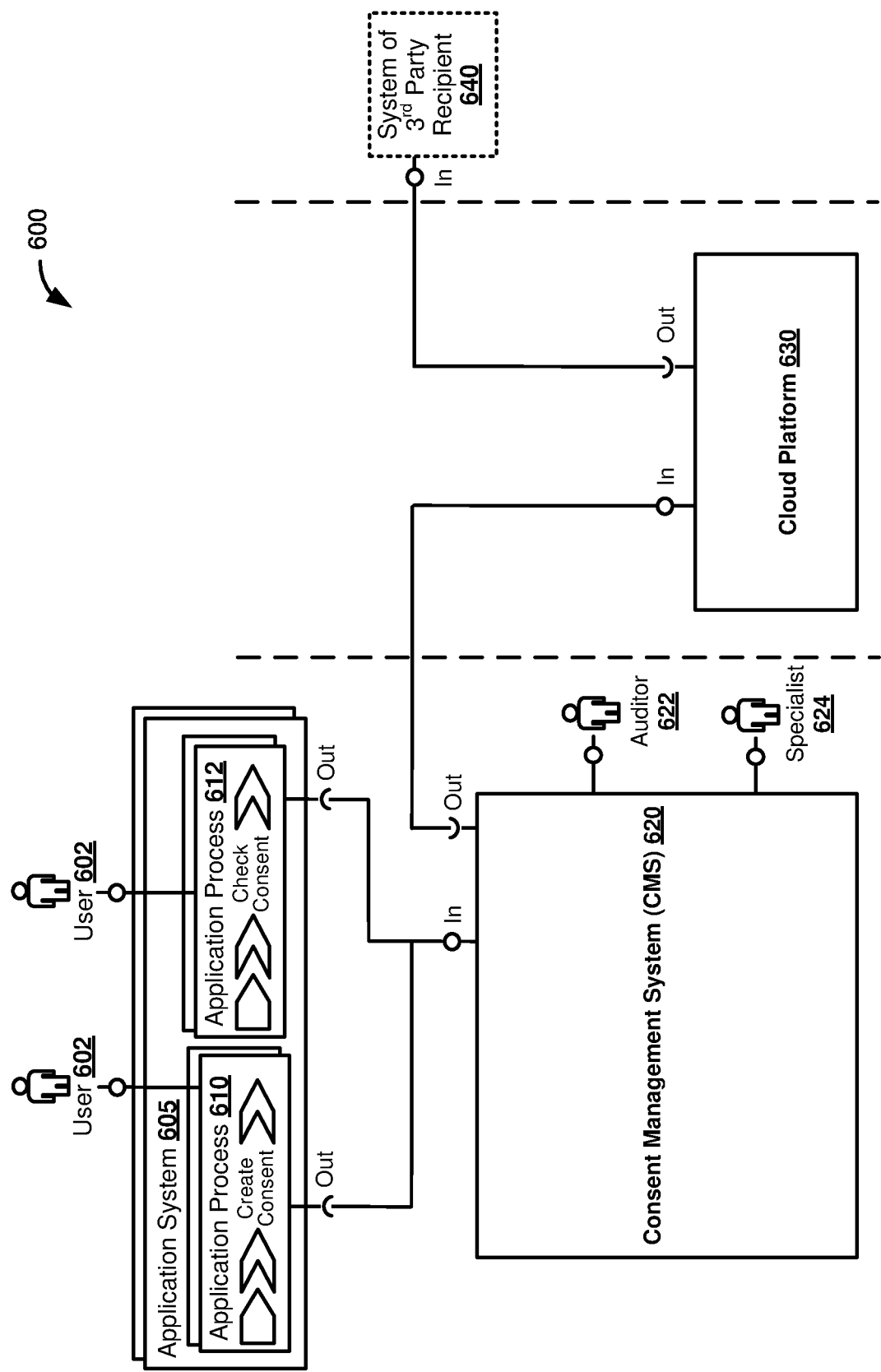
FIG. 6 is a block diagram illustrating a CMS installed as an on-premise system, according to one embodiment.

FIG. 6 illustrates a multi-system landscape 600 including a CMS 620 installed on-premise, according to one embodiment. For example, the CMS 105 described above with reference to FIG. 1 may be installed in a private network of an organization that is a data controller of the CMS 620. The CMS 620 may be deployed on a server connected to the private network of the organization. One or more application systems such as application system 605 may be installed in the private network. In one embodiment, the application system 605 represents a reference to the application system 160 of FIG. 1. The one or more application systems may be deployed on the same server as the CMS 620. Alternatively, the one or more application systems may be deployed and run on other computing platforms such servers, cloud platforms, or personal devices connected to the private network of the organization.

In one embodiment, the CMS 620 is a dedicated system to manage individual consent data records generated by the application systems such as the application system 605. For example, user 602 of the application system 605 may be the data subject. It should be appreciated, however, that the user 602 may not be the data subject. Rather, the user 602 may be legally authorized to create individual consent data records on behalf of one or more data subjects. The application system 605 supports a number of application processes, including application process 610 to create consent and application process 612 to check consent. The number of application processes of the application system 605 can be triggered by authorized users of the application system 605, such as the user 602 (e.g., the data subject). The user 602 may instantiate a consent template such as the consent template 132 of FIG. 1. to create an individual consent data record such as the individual consent data record of FIG. 1. For example, the user 602 may trigger the application process 610 to create the individual consent data record. Further, the user 602 may trigger the application process 612 to check/read individual consent data records associated with the user 602.

In one embodiment, the CMS 620 can be viewed as a central hub for managing individual consent data records within the private network of the organization. When triggered by the user 602, the application process 610 to create consent and the application process 612 to check consent may invoke services provided by the CMS 620 to create the individual consent data record for the user 602 and provide the individual consent data record to the user 602 for viewing. For example, local application programming interfaces (APIs) provided by a number of consent management application components (not illustrated) of the CMS 620 may enable the CMS 620 to provide local services that include storing a number of predefined consent templates, receiving a request to instantiate a consent template of the number of predefined consent templates, create the individual consent data record for the data subject (e.g., the user 602) based on the instantiated consent template, and store the individual consent data record. The number of consent management application components of and corresponding functionality of the CMS 620 are described in detail above with reference to the CMS 105 of FIG. 1.

In one embodiment, a CMS specialist 624 configures and administers the CMS 620. For example, the specialist 624 may define the number of consent templates to be instantiated when the CMS 620 is running. Additionally, the specialist 624 may schedule and run mass-processes such as selecting expiring individual consent data records to send out notification with an option for renewal. For example, the specialist 624 may utilize the functionality of mass-process components 140 of FIG. 1 to schedule and run the mass-processes.

In one embodiment, other authorized users of the CMS 620 such as auditor 622 may access and view individual consent data records stored in the CMS 620. For example, the auditor 622 may view the individual consent data records via the consent viewer 125 of FIG. 1. The consent viewer 125 provides a dedicated UI for selecting, based on criteria, the individual consent data records to be viewed. Examples of criteria for selection of the individual consent data records include, but are not limited to, data controller, data subject, purpose, and template.

In one embodiment, one or more systems of $3^{rd}$ party recipients such as system of $3^{rd}$ party recipient 640 are notified upon creation of the individual consent data record. A $3^{rd}$ party recipient is an external organization to which personal data of the data subject is transferred when the data subject gives consent. Upon creation of the individual consent data record, a copy of the individual consent data record is sent to the system of the $3^{rd}$ party recipient 640. Further, notification messages for expired individual consent data records may be sent to the system of the $3^{rd}$ party recipient 640. For example, the mass-process components 140 may send the notification messages. In one embodiment, the notification messages are routed from the CMS 620 to the system of the $3^{rd}$ party recipient 640 by a secure messaging service provided by cloud platform 630 that is connected with the CMS 620 and with the system of the $3^{rd}$ party recipient 640.

Figure 7:
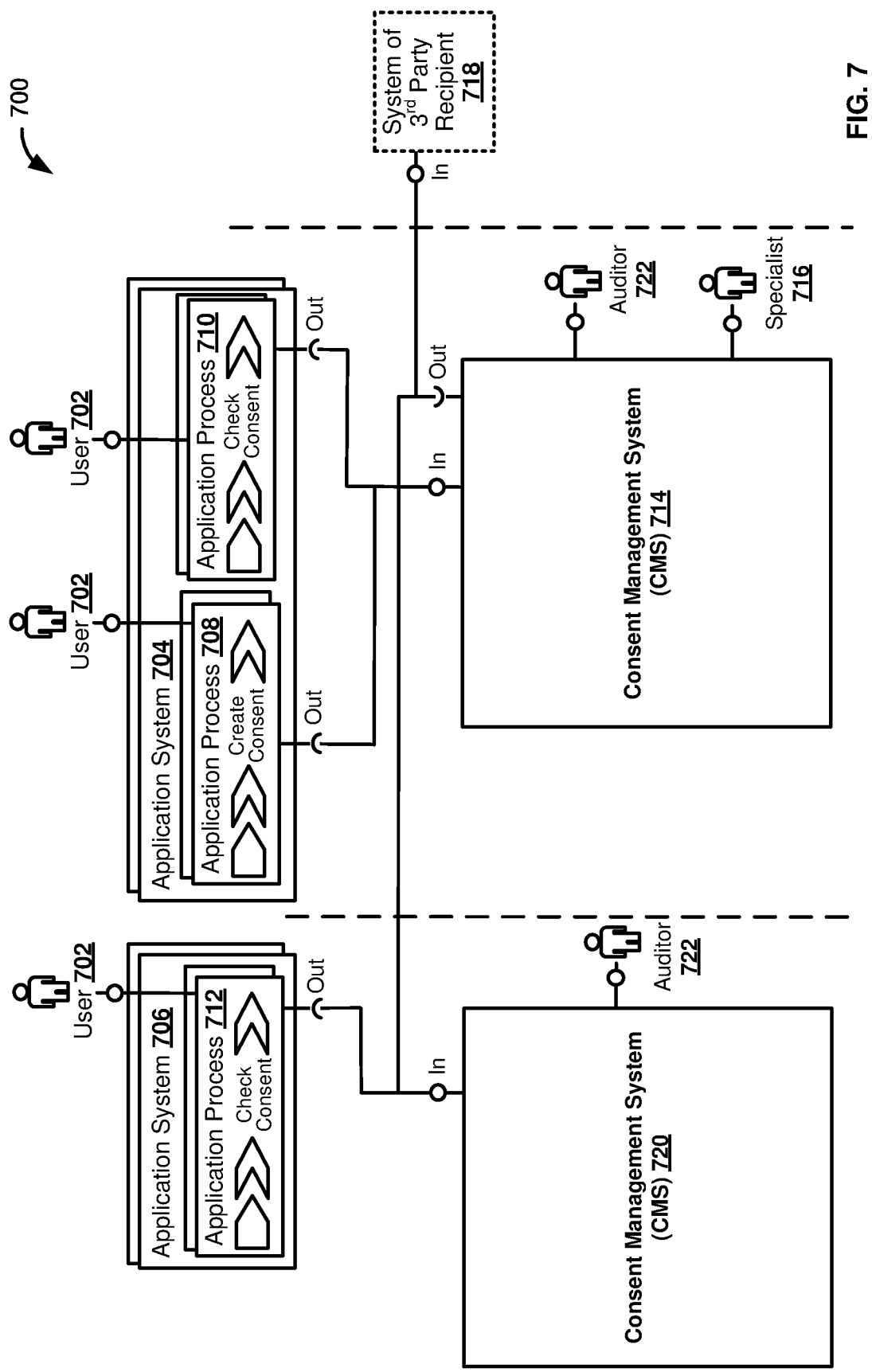
FIG. 7 is a block diagram illustrating a CMS to provide CMS service to tenants of a cloud computing platform, according to one embodiment.

FIG. 7 illustrates a multi-system landscape 700 including CMS 714 and CMS 720, according to one embodiment. The CMS 714 runs on a cloud computing platform (not illustrated) and provides consent as a service (CaaS) to tenants (e.g., the tenants of the computing platform 100 described with reference to FIG. 1) of the cloud computing platform. In one embodiment, the CMS 714 represents the CMS 105 of FIG. 1. that is installed on a cloud computing platform. The CMS 714 can be viewed as a centralized CMS hub for management of individual consent data records, such as the individual consent data record 137 of FIG. 1, generated by a number of application systems, such as application system 704, deployed and running on the cloud computing platform.

In one embodiment, the application system 704 supports a number of application processes, including application process 708 to create individual consent data records and application process 710 to check individual consent data records. The number of application processes of the application system 704 can be triggered by authorized users of the application system 704, such as the user 702. The user 702 may instantiate a consent template (e.g., the consent template 132 of FIG. 1) to create the individual consent data record 137. Thus, the user 702 can be referred to as data subject. It should be appreciated, however, that the user 702 may not be the data subject. Rather, the user 702 may be legally authorized to create individual consent data records on behalf of one or more data subjects. For example, the user 702 may trigger the application process 708 to create the individual consent data record 137. Further, the user 702 may trigger the application process 710 to check/read individual consent data records associated with the user 702.

In one embodiment, CMS specialists, such as specialist 716, configure the CMS 714. The specialist 716 configures one or more consent templates to be instantiated by the application system 704 when creating the individual consent data records for the user 702. Further, the specialist 716 may schedule and run mass-processes such selecting expiring individual consent data records and sending a notification including a renewal option. In addition, other authorized users of the CMS system 714 (e.g., auditor 722) may view the individual consent data records stored in the CMS system 714. In one embodiment, functionalities of the CMS 714 are provided by a number of consent management application components described above with reference to FIG. 1.

In one embodiment, the multi-system landscape 700 includes CMS 720 in addition to the CMS 714. The CMS 720 is running in a private network of a data controller as an on-premise CMS instance. Upon creation of the individual consent data records at the CMS 714, copies of the individual consent data records are sent to the CMS 720. This way, individual consent data records created and stored in the CMS 714 running on the cloud computing platform may be accessed in the on-premise CMS 720. For example, the user 702 may access application system 706 deployed on-premise and check/view the individual consent data records created on the cloud computing platform. Similarly, the auditor 722 may check/view the individual consent data records through either of the CMS 714 or the CMS 720. In one embodiment, since the CMS 720 is configured to receive copies of the individual consent data records created and stored in the CMS 714, the CMS 720 can be referred to as a client CMS of the CMS 714.

In one embodiment, upon creation of the individual consent data record 137, a copy of the individual consent data record 137 is sent to the system of the 3$^{rd}$ party recipient 718. Further, notification messages for expired individual consent data records may be sent the system of the 3$^{rd}$ party recipient 718. For example, the mass-process components 140 of FIG. 1 may send the notification messages. The notification messages are routed from the CMS 714 to the system of the 3$^{rd}$ party recipient 718 by a secure messaging service provided by the cloud computing platform.

Figure 8:
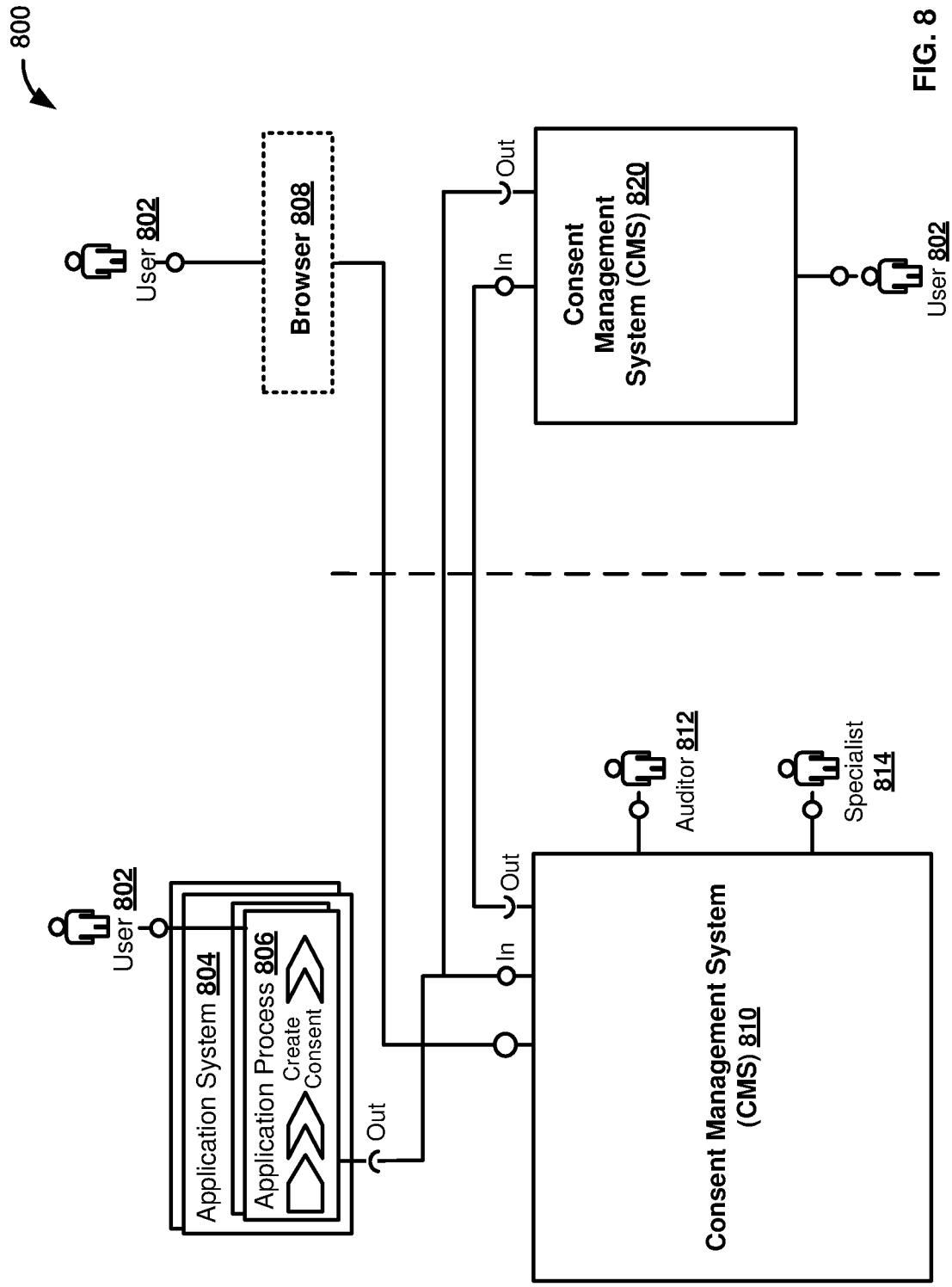
FIG. 8 is a block diagram illustrating a personal consent repository (PCR), according to one embodiment.

FIG. 8 illustrates a multi-system landscape 800 including CMS 810 and a CMS 820, according to one embodiment. The CMS 810 is deployed and runs on a cloud computing platform. The CMS 810 represents a reference to the CMS 714 of FIG. 7. In one embodiment, CMS specialist 814 configures the CMS 810. The specialist 814 configures one or more consent templates, such as the consent template 132 of FIG. 1, to be instantiated by the application system 804 when creating individual consent data records for the user 802. In one embodiment, user 802 may be the data subject. It should be appreciated, however, that the user 802 may not be the data subject. Rather, the user 802 may be legally authorized to create individual consent data records on behalf of one or more data subjects. Further, the specialist 814 may schedule and run mass-processes such as selecting expiring individual consent data records and sending a notification including a renewal option. In addition, other authorized users of the CMS 810 (e.g., auditor 812) may view the individual consent data records stored in the CMS 810.

In one embodiment, user 802 triggers application process 806 of application system 804 to create and store an individual consent data record (e.g., the individual consent data record 137 of FIG. 1) in the CMS 810. The user 802 can be referred to as a data subject for whom the individual consent data record 137 is created. Upon creation of the individual consent data record 137, the user 802 may access the CMS 810 via browser 808. Thus, the user 802 may view, renew, or withdraw the corresponding individual consent data record 137 via the browser 808.

In one embodiment, the CMS 810 is coupled with a CMS 820. The CMS 820 is installed on a personal device computer platform such as a personal computer or mobile device. A CMS running on a personal device may be referred to as personal consent repository (PCR). The user 802 may access the CMS 820, connect to the CMS 810 that stores the individual consent data records, and check/view the individual consent data records associated with the user 802. Optionally, the user 802 may download the individual consent data records associated with the user 802 to the CMS 820. The user 802 may manage the downloaded individual consent data records through the CMS 820. For example, the user 802 may receive a notification for an expiring individual consent data record at the CMS 820, and agree/disagree to renew the individual consent data record. Further, the user 802 may withdraw a given consent via the CMS 820.

Figure 9:
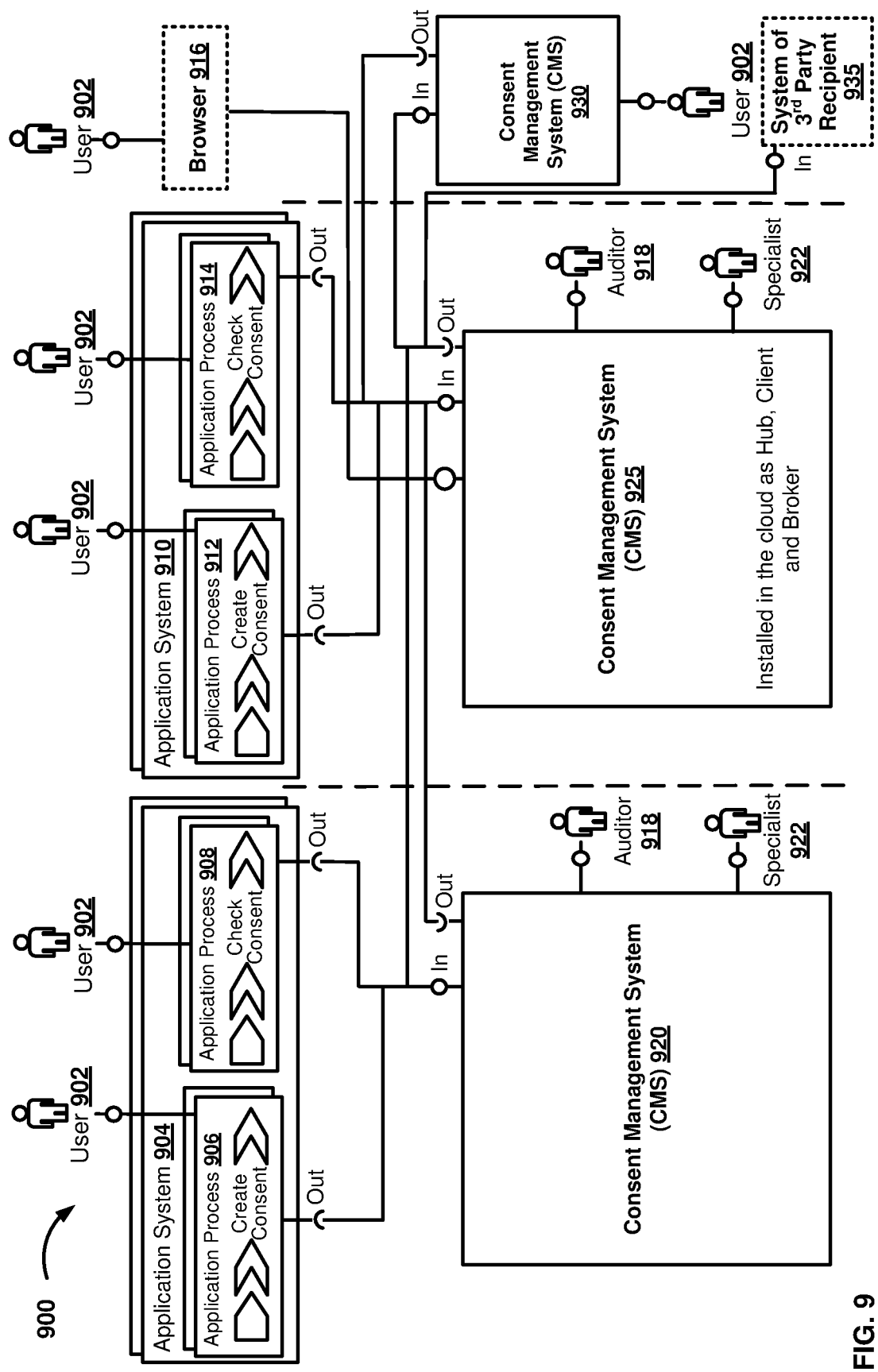
FIG. 9 is a block diagram illustrating a comprehensive CMS including an on-premise CMS, a cloud platform CMS, and a PCR, according to one embodiment.

FIG. 9 illustrates a multi-system landscape 900 that includes a comprehensive CMS, according to one embodiment. The comprehensive CMS includes CMS 920 running on an on-premise computing platform (not illustrated), a CMS 925 (e.g., CaaS) running on a cloud computing platform (not illustrated), and a CMS 930 running on a personal device computing platform (not illustrated) as a PCR. The CMS instances 920, 925, and 930 maintain and exchange individual consent data records, such as the individual consent data record 137 of FIG. 1, of data subjects (e.g., user 902). In one embodiment, the CMS 105 of FIG. 1 is installed and runs on the on-premise computing platform as the CMS 920, on the cloud computing platform as the CMS 925, and on the personal device computing platform as the CMS 930.

In one embodiment, the CMS 920 represents a centralized consent management hub for one or more on-premise application systems such as application system 904. In accordance with an application process triggered by the user 902 (e.g., application process 906 to create consent, application process 908 to check consent, etc.), the application system 604 may create an individual consent data record (e.g., the individual consent data record 137 of FIG. 1) or read the individual consent data record 137. When the individual consent data record 137 includes transfer of personal data to 3rd party recipient, a notification message is sent to the system of the 3rd party recipient 935. The notification message may include a copy of the individual consent data record 137. In one embodiment, CMS specialists such as specialist 922 access the CMS 920 to configure consent templates, such as the consent template 132 of FIG. 1, or new versions of consent templates that may be instantiated when the application system is running. Further, the specialist 922 may schedule and run mass-processes when necessary. For example, the specialist 922 may select a large number of expiring individual consent data records and send notifications. In addition, authorized users such as auditor 918 may check/view individual consent data records of data subjects.

In one embodiment, the CMS 925 represents a centralized consent management hub for one or more application systems running on a cloud computing platform such as application system 910. The CMS 925 provides similar functionalities as the CMS 920. Further, the CMS 925 operates as a consent client. That is, the CMS 925 receives and stores copies of individual consent data records created at the CMS 920. In one embodiment, the CMS 925 operates as a consent client system to the CMS 920 and vice versa. Thus, individual consent data records stored in the CMS 920 and the CMS 925 are synchronized. Such a configuration allows for individual consent data records of a data subject to be accessed in the CMS 925 and viewed, renewed, or withdrawn by the data subject via browser 916. Copies of individual consent data records originally created in CMS 920 may be viewed in CMS 925 by data subjects or by 3rd parties. Thus, the data subjects or the 3$^{rd}$ parties may view the individual consent records from outside of the internal network of the data controller. In addition, by providing copies of the individual consent data records to the CMS 920 and the CMS 925, on-premise application systems may access the individual consent data records without calling the CMS 925.

In one embodiment, individual consent data records may be changed in the CMS, where they have been originally created. Thus, requests to change individual consent data records are forwarded to the original CMS, either CMS 920 or CMS 925. Further, the CMS 925 may send notifications to 3$^{rd}$ party recipient systems such as the 3$^{rd}$ party recipient system 935 and forward notifications from the CMS 920 to the 3$^{rd}$ party recipient system 935.

In one embodiment, the individual consent data records can be accessed by the data subjects (e.g., the user 902) to view, renew, or withdraw the individual consent records through browser 916 as described above. Alternatively, the CMS 930 operating as a PCR may be installed on a personal device of a data subject such as the user 902 to enable communication with the CMS 925, and thus provide a functionality to download, store, and view copies of individual consent data records associated with the user 902.

Figure 10:
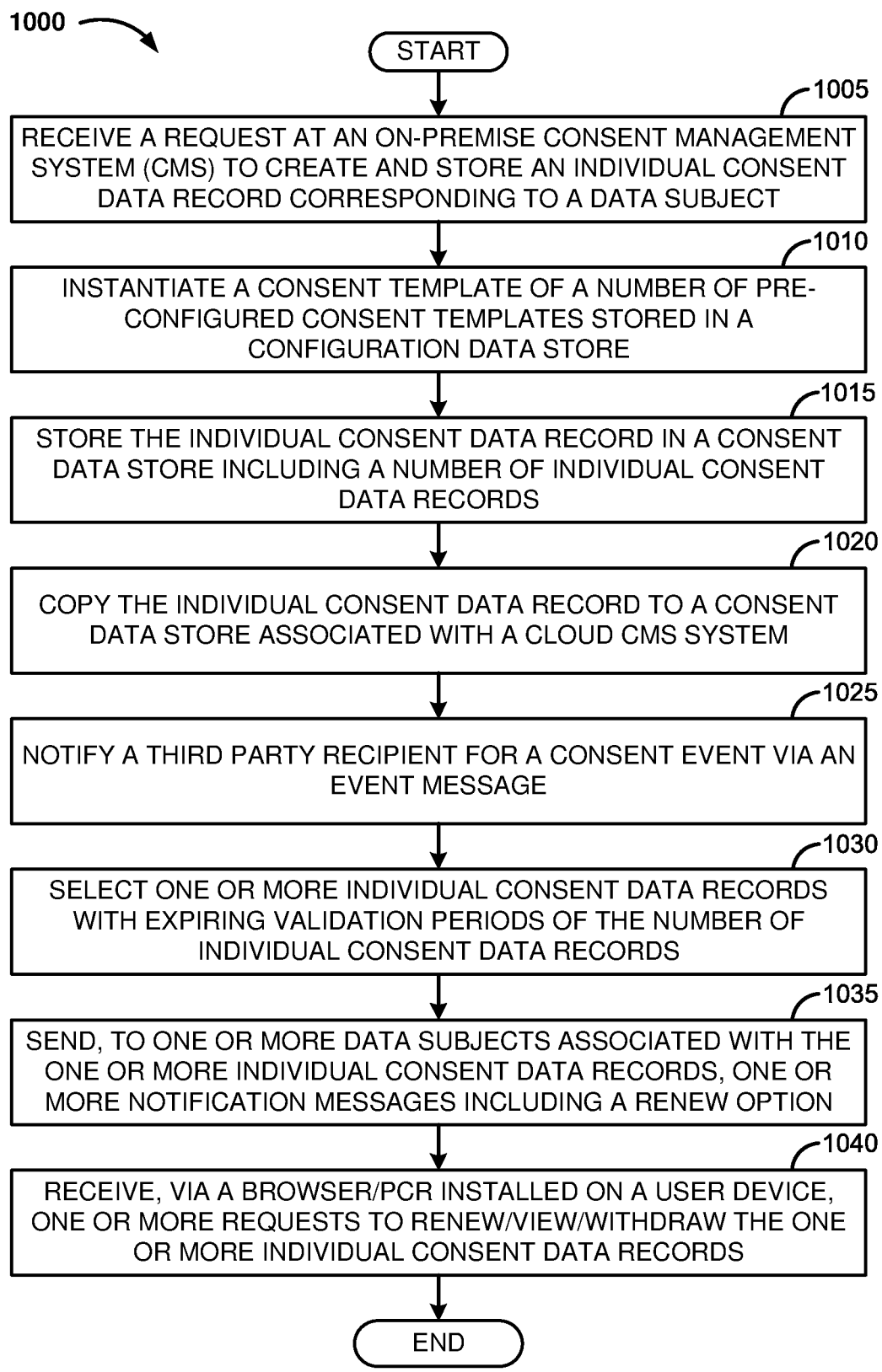
FIG. 10 is a flow diagram illustrating a process to create a consent record in an on-premise CMS, according to one embodiment.

FIG. 10 illustrates a process 1000 to create an individual consent data record in an on-premise CMS system, according to one embodiment. For example, the individual consent data record 137 of FIG. 1 may be created in accordance with the process 1000. At 1005, a request to create and store the individual consent data record is received at the on-premise CMS. The individual consent data record corresponds to a data subject. The data subject may be a user of an application system, such as the user 102 of FIG. 1. The individual consent data record may be associated with consent given for processing of personal data of the user in relation to the application system. the data subject gives consent to the application system to process data associated with the data subject, such as personal data of the data subject, in association with a functionality of the application system. At 1010, a consent template from a number of consent templates is instantiated to create the individual consent data record. For example, the consent template 132 of FIG. 1 may be instantiated by the application system when the user accesses the application system. In one embodiment, the number of consent templates is pre-configured in a configuration data store. Upon creation, at 1015, the individual consent data record is stored in a consent data store associated with the on-premise CMS system. The consent data store includes a number of individual consent data records.

At 1020, the individual consent data record is copied to a consent data store associated with a cloud CMS system. This way, individual consent data records created and stored in the on-premise CMS may be accessed in the cloud CMS. For example, the data subject may access an application system deployed in the cloud and check/view the individual consent data records created in the on-premise CMS. Similarly, an auditor may check/view the individual consent data records through either of the on-premise CMS or the cloud CMS. In one embodiment, since the cloud CMS is configured to receive copies of the individual consent data records created and stored in the on-premise CMS, the cloud CMS can be referred to as a client CMS of the on-premise CMS.

In one embodiment, the individual consent record includes a consent to transfer personal data, associated with the individual consent data record, of the data subject to a $3^{rd}$ party recipient. Thus, at 1025, a copy of the individual consent data record is sent in an event message to notify the $3^{rd}$ party recipient for a consent event (e.g., creation of the individual consent data record). At 1030, one or more individual consent data records with expiring validation periods are selected from the number of individual consent data records. At 1035, one or more notification messages are sent to one or more data subjects associated with the one or more individual consent data records. The one or more notification messages include an option to renew the one or more individual consent data records. At 1040, one or more requests to renew/view/withdraw the one or more individual consent data records are received. The one or more request may be received via a browser or a PCR installed on a personal device of a data subject.

Figure 11:
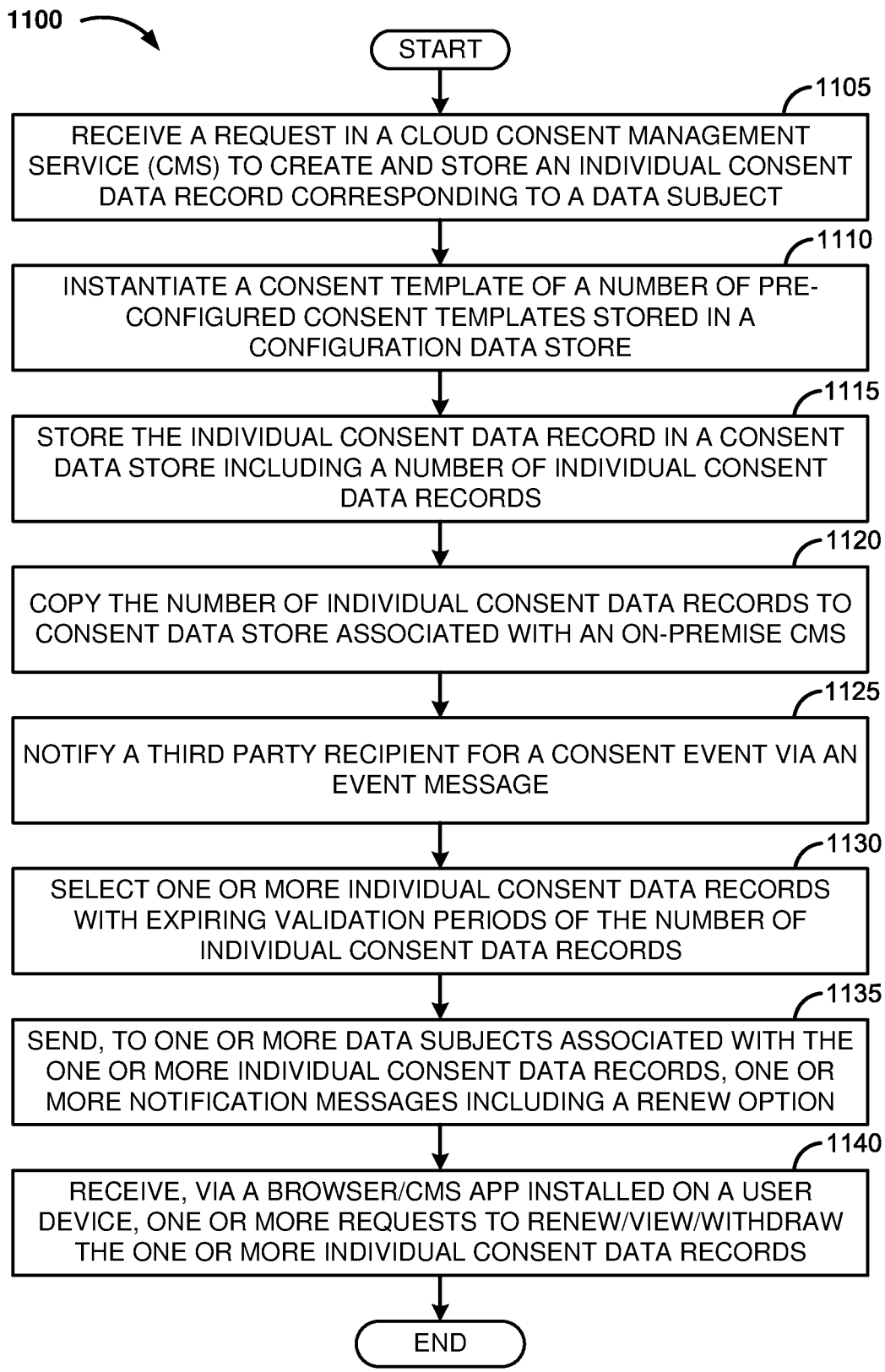
FIG. 11 is a flow diagram illustrating a process to create a consent record in a cloud CMS, according to one embodiment.

FIG. 11 illustrates a process 1100 to create an individual consent data record in cloud CMS, according to one embodiment. At 1105, a request to create and store the individual consent data record is received at the cloud CMS. The individual consent data record corresponds to a data subject.

At 1110, a consent template from a number of consent templates is instantiated to create the individual consent data record. In one embodiment, the number of consent templates is pre-configured in a configuration data store. Upon creation, at 1115, the individual consent data record is stored in a consent data store associated with the cloud CMS. The consent data store includes a number of individual consent data records.

At 1120, the individual consent data record is copied to a consent data store associated with an on-premise CMS. This way, individual consent data records created and stored in the cloud CMS may be accessed in the on-premise CMS. For example, the data subject may access an application system deployed on-premise and check/view the individual consent data records created in the cloud CMS. Similarly, an auditor may check/view the individual consent data records through either of the cloud CMS or the on-premise CMS. In one embodiment, since the on-premise CMS is configured to receive copies of the individual consent data records created and stored in the cloud CMS, the on-premise CMS can be referred to as a client CMS of the cloud CMS.

In one embodiment, the individual consent data record includes a consent to transfer personal data, associated with the individual consent data record, of the data subject to a $3^{rd}$ party recipient. Thus, at 1125, a copy of the individual consent data record is sent in an event message to notify the $3^{rd}$ party recipient for a consent event (e.g., creation of the individual consent data record). At 1130, one or more individual consent data records with expiring validation periods are selected from the number of individual consent data records. At 1135, one or more notification messages are sent to one or more data subjects associated with the one or more individual consent data records. The one or more notification messages include an option to renew the one or more individual consent data records. At 1140, one or more requests to renew/view/withdraw the one or more individual consent data records are received. The one or more request may be received via a browser or a PCR installed on a personal device of a data subject.

Some embodiments may include the above-described methods being written as one or more software components. These components, and the functionality associated with each, may be used by client, server, distributed, or peer computer systems. These components may be written in a computer language corresponding to one or more programming languages such as, functional, declarative, procedural, object-oriented, lower level languages and the like. They may be linked to other components via various application programming interfaces and then compiled into one complete application for a server or a client. Alternatively, the components maybe implemented in server and client applications. Further, these components may be linked together via various distributed programming protocols. Some example embodiments may include remote procedure calls being used to implement one or more of these components across a distributed programming environment. For example, a logic level may reside on a first computer system that is remotely located from a second computer system containing an interface level (e.g., a graphical user interface). These first and second computer systems can be configured in a server-client, peer-to-peer, or some other configuration. The clients can vary in complexity from mobile and handheld devices, to thin clients and on to thick clients or even other servers.

The above-illustrated software components are tangibly stored on a computer readable storage medium as instructions. The term "computer readable storage medium" should be taken to include a single medium or multiple media that stores one or more sets of instructions. The term "computer readable storage medium" should be taken to include any physical article that is capable of undergoing a set of physical changes to physically store, encode, or otherwise carry a set of instructions for execution by a computer system which causes the computer system to perform any of the methods or process steps described, represented, or illustrated herein. A computer readable storage medium may be a non-transitory computer readable storage medium. Examples of a non-transitory computer readable storage media include, but are not limited to: magnetic media, such as hard disks, floppy disks, and magnetic tape; optical media such as CD-ROMs, DVDs and holographic devices; magneto-optical media; and hardware devices that are specially configured to store and execute, such as application-specific integrated circuits ("ASICs"), programmable logic devices ("PLDs") and ROM and RAM devices. Examples of computer readable instructions include machine code, such as produced by a compiler, and files containing higher-level code that are executed by a computer using an interpreter. For example, an embodiment may be implemented using Java, C++, or other object-oriented programming language and development tools. Another embodiment may be implemented in hard-wired circuitry in place of, or in combination with machine readable software instructions.

Figure 12:
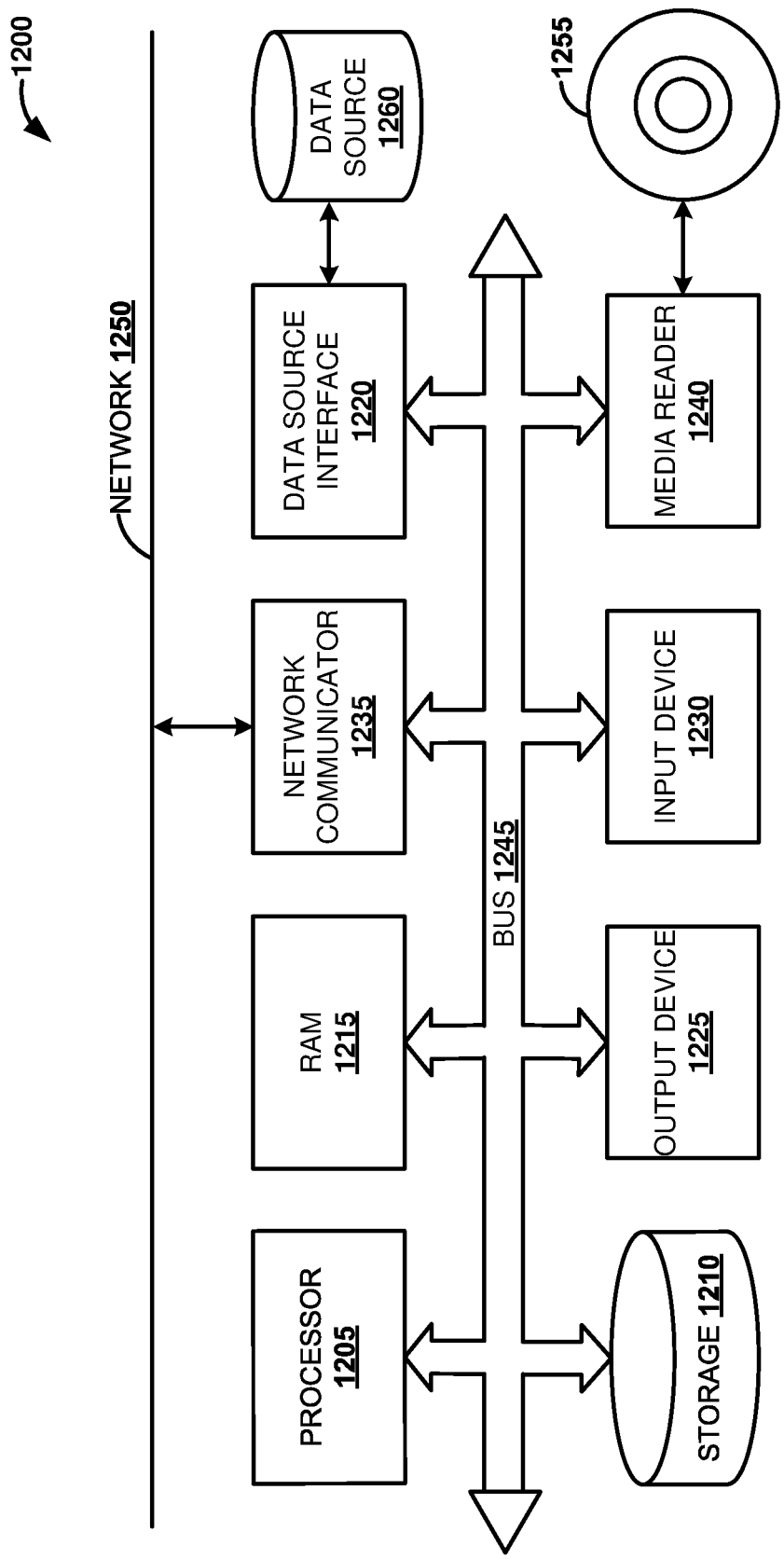
FIG. 12 is a block diagram of an exemplary computer system, according to one embodiment.

FIG. 12 is a block diagram of an exemplary computer system 1200. The computer system 1200 includes a processor 1205 that executes software instructions or code stored on a computer readable storage medium 1255 to perform the above-illustrated methods. The processor 1205 can include a plurality of cores. The computer system 1200 includes a media reader 1240 to read the instructions from the computer readable storage medium 1255 and store the instructions in storage 1210 or in random access memory (RAM) 1215. The storage 1210 provides a large space for keeping static data where at least some instructions could be stored for later execution. According to some embodiments, such as some in-memory computing system embodiments, the RAM 1215 can have sufficient storage capacity to store much of the data required for processing in the RAM 1215 instead of in the storage 1210. In some embodiments, all of the data required for processing may be stored in the RAM 1215. The stored instructions may be further compiled to generate other representations of the instructions and dynamically stored in the RAM 1215. The processor 1205 reads instructions from the RAM 1215 and performs actions as instructed. According to one embodiment, the computer system 1200 further includes an output device 1225 (e.g., a display) to provide at least some of the results of the execution as output including, but not limited to, visual information to users and an input device 1230 to provide a user or another device with means for entering data and/or otherwise interact with the computer system 1200. Each of these output devices 1225 and input devices 1230 could be joined by one or more additional peripherals to further expand the capabilities of the computer system 1200. A network communicator 1235 may be provided to connect the computer system 1200 to a network 1250 and in turn to other devices connected to the network 1250 including other clients, servers, data stores, and interfaces, for instance. The modules of the computer system 1200 are interconnected via a bus 1245. Computer system 1200 includes a data source interface 1220 to access data source 1260. The data source 1260 can be accessed via one or more abstraction layers implemented in hardware or software. For example, the data source 1260 may be accessed by network 1250. In some embodiments the data source 1260 may be accessed via an abstraction layer, such as, a semantic layer.

A data source is an information resource. Data sources include sources of data that enable data storage and retrieval. Data sources may include databases, such as, relational, transactional, hierarchical, multi-dimensional (e.g., OLAP), object oriented databases, and the like. Further data sources include tabular data (e.g., spreadsheets, delimited text files), data tagged with a markup language (e.g., XML data), transactional data, unstructured data (e.g., text files, screen scrapings), hierarchical data (e.g., data in a file system, XML data), files, a plurality of reports, and any other data source accessible through an established protocol, such as, Open Data Base Connectivity (ODBC), produced by an underlying software system (e.g., ERP system), and the like. Data sources may also include a data source where the data is not tangibly stored or otherwise ephemeral such as data streams, broadcast data, and the like. These data sources can include associated data foundations, semantic layers, management systems, security systems and so on.

In the above description, numerous specific details are set forth to provide a thorough understanding of embodiments. One skilled in the relevant art will recognize, however that the embodiments can be practiced without one or more of the specific details or with other methods, components, techniques, etc. In other instances, well-known operations or structures are not shown or described in detail.

Although the processes illustrated and described herein include series of steps, it will be appreciated that the different embodiments are not limited by the illustrated ordering of steps, as some steps may occur in different orders, some concurrently with other steps apart from that shown and described herein. In addition, not all illustrated steps may be required to implement a methodology in accordance with the one or more embodiments. Moreover, it will be appreciated that the processes may be implemented in association with the apparatus and systems illustrated and described herein as well as in association with other systems not illustrated.

The above descriptions and illustrations of embodiments, including what is described in the Abstract, is not intended to be exhaustive or to limit the one or more embodiments to the precise forms disclosed. While specific embodiments of, and examples for, the one or more embodiments are described herein for illustrative purposes, various equivalent modifications are possible within the scope, as those skilled in the relevant art will recognize. These modifications can be made in light of the above detailed description. Rather, the scope is to be determined by the following claims, which are to be interpreted in accordance with established doctrines of claim construction.

What is claimed is:

1. A computer implemented method to manage consent data records, the method comprising:
    instantiating a consent template selected from a plurality of consent templates to create a consent data record at an on-premise consent management system (CMS) associated with a plurality of on-premise application systems running on an on-premise platform, wherein the consent data record is associated with a data controller, a first data subject, a data record, a validation period, and a first application system from the plurality of on-premise application systems related to the data record;
    storing the consent data record at the on-premise CMS, wherein the on-premise CMS comprises a plurality of consent data records associated with data subjects, wherein a first set of consent data records from the plurality of consent data records is associated with the first data subject from the data subjects and one or more on-premise application systems from the plurality of on-premise application systems;

receiving and storing consent data records from the on-premise CMS at a centralized consent management hub system running at a cloud platform, wherein the centralized consent management hub system is associated with a plurality of cloud application systems, and wherein the centralized consent management hub system stores consent data records associated with the first data subject and the one or more on-premise application systems and one or more cloud application systems from the plurality of cloud application systems;

enabling access to the plurality of consent data records through the centralized consent management hub system deployed on the cloud platform;

receiving a request at the centralized consent management hub system to view a consent data record from the plurality of consent data records associated with the first data subject and an application system from the one or more on-premise application systems and one or more cloud application systems from the plurality of cloud application systems;

based on an evaluation of validation periods of the consent data records associated with the first data subject and stored at the centralized consent management hub system, sending, through a personal consent repository application of the first data subject accessed through a user device, a first notification for expiration of a first record from the consent data records, wherein the personal consent repository application is coupled to the centralized consent management hub system;

receiving from the user device, a request for withdrawal of the first record, wherein the request is provided through an interface comprised in the first notification for expiration of the first record; and providing a second notification from the centralized consent management hub system to the associated application system that the first record defining consent by the first data subject for the associated application system has been withdrawn.

2. The method of claim 1, further comprising:
defining a data model for the consent template to comprise one or more attributes; and
preconfiguring an attribute from the one or more attributes with a default attribute value for creation of the consent data record at the on-premise CMS, wherein the consent data record defines authorized purpose to process personal data from the data record associated with the data subject.

3. The method of claim 1, further comprising:
when the consent data record defines an authorization for transferring of personal data comprised in the data record from the first application system associated with the data record to a third-party application system, sending a copy of the consent data record from the on-premise CMS to the third-party application system.

4. The method of claim 1, further comprising:
copying the plurality of consent data records to a consent data store associated with the centralized consent management hub system deployed on the cloud platform; and
enabling access to the plurality of consent data records through the centralized consent management hub system deployed on the cloud platform to an application system running on the cloud platform; and receiving a request at the centralized consent management hub system to view a consent data record from the plurality.

5. The method of claim 4, further comprising:
synchronizing the on-premise CMS and the centralized consent management hub system deployed on the cloud platform to include identical sets of consent data records.

6. The method of claim 4, further comprising:
filtering, based on criteria, the plurality of consent data records to determine one or more of the plurality of consent data records, wherein the criteria is provided with the received request; and
providing the one or more of the plurality of consent data records at a display screen.

7. The method of claim 1, further comprising:
receiving a request from a user interface (UI) application coupled to the on-premise CMS, the request being associated with the data subject; and
providing the plurality of consent data records at the UI application.

8. A computer system to manage consent data, the system comprising:
a processor; and
a memory in association with the processor storing instructions related to:
a consent management configuration module at a central consent management system (CMS) hub that provides a first application programming interface (API) to:
define a data model for a consent template comprising one or more attributes;
preconfigure an attribute from the one or more attributes with a default attribute value to create a consent data record at the central CMS hub, the consent data record being associated with a data controller, a first data subject, a data record, a validation period, an application system related to the data record, and an authorized purpose for processing personal data from the data record associated with the first data subject; and
a consent management core module at the central CMS hub that provides a second API to instantiate the consent template and create the consent data record associated with a data subject to be stored at a consent data store at the central CMS hub, wherein the consent data store comprises a plurality of consent data records associated correspondingly with a plurality of data subjects and with a plurality of corresponding application systems, wherein the plurality of corresponding application systems comprises the application system, and wherein the central CMS hub is associated with a plurality of cloud application systems and a plurality of on-premise application systems, wherein the CMS hub stores consent data records associated with the first data subject and one or more on-premise application systems of the plurality of on-premise application systems and one or more cloud application systems from the plurality of cloud application systems, and wherein the central CMS hub is configured to:
provide access to the plurality of consent data records;

receive a request to view a consent data record from the plurality of consent data records associated with the first data subject and an application system from the one or more on-premise application systems and one or more cloud application systems from the plurality of cloud application systems;

receive, from a user device, a request for withdrawal of a first record from the plurality of consent data records, wherein the request is provided through an interface comprised in a first notification for expiration of the first record to request a renewal of the first record, wherein the first notification for the expiration of the first record is provided from the central CMS hub through a personal consent repository application accessed through the user device; and providing a second notification to the associated application system that the first record defining consent by the first data subject for the associated application system has been withdrawn.

9. The system of claim 8, wherein the memory stores instructions related to:

a consent viewer module associated with the consent management core module, wherein the consent viewer module includes instructions to:

receive a request at the central CMS hub to view a consent data record from the plurality, wherein the request is received from an application running at a computing platform hosting the central CMS hub, and the request being associated with consent data associated with an application system running on a different computing platform;

filter, based on criteria, the plurality of consent data records to determine one or more of the plurality of consent data records, wherein the criteria is provided with the received request; and provide the one or more of the plurality of consent data records at a display screen.

10. The system of claim 8, wherein the memory stores instructions related to:

a consent mass-process module coupled to the consent management core module to:

evaluate validation periods of the consent data records associated with the first data subject and stored at the central CMS hub; and send, through the personal consent repository application of the first data subject accessed through the user device, the notification for expiration of the first record from the plurality of consent data records; and provide, at the user device, an interface comprised in the first notification to request a renewal of the first record.

11. The system of claim 8, wherein the consent management core module comprises instructions to receive a request associated with the data subject from a user interface (UI) application coupled to the central CMS hub and to provide the plurality of consent data records at the UI application.

12. The system of claim 8, wherein the memory comprises a consent event handler module comprising instructions to receive a request associated with managing the consent data record and to forward the request to the consent management core module.

13. The system of claim 12, wherein the consent event handler module comprises instructions to receive a request to withdraw the consent data record and to forward the request to withdraw the consent data record to the consent management core module, wherein the consent data record is marked as withdrawn by the consent management core module.

14. A non-transitory computer readable medium storing instructions which when executed by at least processor cause a computer system to perform operations comprising:

instantiate a consent template selected from a plurality of consent templates to create a consent data record at an on-premise consent management system (CMS) associated with a plurality of on-premise application systems running on an on-premise platform, wherein the consent data record is associated with a data controller, a first data subject, a data record, a validation period, and a first application system from the plurality of on-premise application systems related to the data record;

store the consent data record at the on-premise CMS, wherein the on-premise CMS comprises a plurality of consent data records associated with data subjects, wherein a first set of consent data records from the plurality of consent data records is associated with the first data subject from the data subjects and one or more on-premise application systems from the plurality of on-premise application systems;

receive and store consent data records from the on-premise CMS at a centralized consent management hub system running at a cloud platform, wherein the centralized consent management hub system is associated with a plurality of cloud application systems, and wherein the centralized consent management hub system stores consent data records associated with the first data subject and the one or more on-premise application systems and one or more cloud application systems from the plurality of cloud application systems;

enable access to the plurality of consent data records through the centralized consent management hub system deployed on the cloud platform;

receive a request at the centralized consent management hub system to view a consent data record from the plurality of consent data records associated with the first data subject and an application system from the one or more on-premise application systems and one or more cloud application systems from the plurality of cloud application systems;

based on an evaluation of validation periods of the consent data records associated with the first data subject and stored at the centralized consent management hub system, send, through a personal consent repository application of the first data subject accessed through a user device, a first notification for expiration of a first record from the consent data records, wherein the personal consent repository application is coupled to the centralized consent management hub system;

receive from the user device, a request for withdrawal of the first record, wherein the request is provided through an interface comprised in the first notification for expiration of the first record to request a renewal of the first record; and provide a second notification from the centralized consent management hub system to the associated application system that the first record defining consent by the first data subject for the associated application system has been withdrawn.

15. The computer readable medium of claim 14, further storing instructions to:

define a data model for the consent template to comprise one or more attributes; and preconfigure an attribute from the one or more attributes with a default attribute value for creation of the consent data record at the on-premise CMS, wherein the consent data record defines authorized purpose to process personal data from the data record associated with the data subject.

16. The computer readable medium of claim 14, further storing instructions to:

when the consent data record defines an authorization for transferring of personal data comprised in the data record from the first application system associated with the data record to a third-party application system, send a copy of the consent data record from the on-premise CMS to the third-party application system.

17. The computer readable medium of claim 14, further storing instructions to:

copy the plurality of consent data records to a consent data store associated with the centralized consent management hub system deployed on the cloud platform; and enable access to the plurality of consent data records through the centralized consent management hub system deployed on the cloud platform to an application system running on the cloud platform; and receive a request at the centralized consent management hub system to view a consent data record from the plurality.

18. The computer readable medium of claim 17, further storing instructions to:

synchronizing the on-premise CMS and the centralized consent management hub system deployed on the cloud platform to include identical sets of consent data records.

19. The computer readable medium of claim 14, further storing instructions to:

filter, based on criteria, the plurality of consent data records to determine one or more of the plurality of consent data records, wherein the criteria is provided with the received request; and provide the one or more of the plurality of consent data records at a display screen.

20. The computer readable medium of claim 14, further storing instructions to:

receive a request from a user interface (UI) application coupled to the on-premise CMS, the request being associated with the data subject; and provide the plurality of consent data records at the UI application.

* * * * *